United States Patent [19]

Ploner et al.

[11] 3,962,344
[45] June 8, 1976

[54] PROCESS FOR MAKING 1,3-DIENE HYDROCARBONS

[75] Inventors: Klaus-Jurgen Ploner, Greifensee; Jost Wild, Uster; Trudi Sigg-Grutter, Winterthur, all of Switzerland

[73] Assignee: Givaudan Corporation, Clifton, N.J.

[22] Filed: May 14, 1974

[21] Appl. No.: 469,918

[30] Foreign Application Priority Data
May 18, 1973 Switzerland.......................... 7122/73

[52] U.S. Cl. ...................... 260/601 R; 260/486 R; 260/488 H; 260/489; 260/614 R; 260/617 R; 260/677 R; 260/680 R; 252/431 N; 252/522
[51] Int. Cl.$^2$.......................................... C07C 47/20
[58] Field of Search............ 252/431 N; 260/680 R, 260/601 R, 614 R, 617 R, 489, 488 H

[56] References Cited
UNITED STATES PATENTS
3,549,679  12/1970  Kappeler et al. .................... 260/489
3,830,833  8/1974  Mabuchi et al. ..................... 260/489

OTHER PUBLICATIONS
Harrod, et al., Homogeneous Catalipis, J. Amer. Chem. Soc., vol. 86, pp. 1776–1779, (1963).
Shukla, Complexes Du Rhodium en Solution Aqueuse, Aunles De Chemie, 6, 1387–1389, (1961).
Cotton, et al., Advanced Inorganic Chem., Interscience Publishers, p. 792, (1966).

Primary Examiner—James O. Thomas, Jr.
Assistant Examiner—G. Breitenstein
Attorney, Agent, or Firm—Thomas Cifelli, Jr.

[57] ABSTRACT

Unsaturated compounds of the general formula:

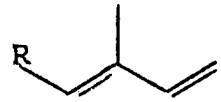

wherein R is defined hereinafter are prepared.

9 Claims, No Drawings

PROCESS FOR MAKING 1,3-DIENE HYDROCARBONS

FIELD OF THE INVENTION

This invention relates to a process for making odorants or intermediates for odorants.

SUMMARY OF THE INVENTION

Compounds of the formula:

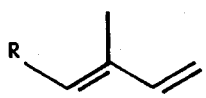
(I)

wherein R represents the ethyl group or a grouping of the formula $(CH_3)_2C=CH-CH_2-$, $(CH_3)_2C=CH-CH_2-CH_2-\underset{\underset{CH_3}{|}}{C}=CH-CH_2-$, $(CH_3)_2\underset{\underset{OR^1}{|}}{C}-CH_2-CH_2-$, $CH_3-\underset{\underset{CHO}{|}}{C}=CH-CH_2-CH_2-\underset{\underset{CH_3}{|}}{C}=CH-CH_2-$, $R^2OCH_2-CH_2-$ or $R^3OCO-CH_2-$ in which $R^1$ represents a hydrogen atom or a lower alkyl or lower acyl group, $R^2$ represents a lower alkyl or lower acyl group and $R^3$ represents a lower alkyl group, are prepared by treating a compound of the general formula

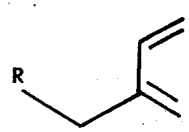
(II)

wherein R has the significance given earlier, or cis-ocimene in the presence of an alcohol with $Rh(NO_3)_3$, $RhCl_3$.aq. or $H_2IrCl_6$ and a carboxylic acid chloride.

The unsaturated hydrocarbons of formula I are valuable as odorants or as intermediates for the preparation of odorants. In contrast to the starting materials they are distinguished by a finer odorant note. In particular, the present process enables ocimene containing a high content of the trans isomer to be manufactured. This is advantageous for the olfactory properties of the product.

DESCRIPTION OF THE PREFERRED EMBODIMENTS

As used in this description and in the claims appended hereto, the term "lower" denotes that the groups prefixed thereby preferably contain up to 6 carbon atoms. Examples of lower alkyl groups are methyl, ethyl, propyl and isopropyl, and examples of lower acyl groups are lower alkanoyl groups such as acetyl, propionyl and butyryl.

Examples of starting materials of formula II include, in particular, myrcene, myrcenol, esters and ethers thereof, β-farnesene and β-sinensal.

In a preferred embodiment of the present invention, myrcene, cis-ocimene or a mixture of cis- and trans-ocimene with a trans content of less than 60 percent is used as the starting material.

The process provided by the present invention can be carried out under careful conditions; for example, at 0° – 50°C. As the alcohol there can be used, for example, a lower aliphatic alcohol such as ethanol, propanol, tertbutanol etc., but especially a secondary lower aliphatic alcohol such as isopropanol or secbutanol. Examples of carboxylic acid chlorides which can be used are aromatic carboxylic acid chlorides, e.g. benzoyl chloride, toluoyl chloride and nitrobenzoyl chlorides) and lower aliphatic carboxylic acid chlorides (e.g. crotonoyl chloride, acrylyl chloride, butyryl chloride, propionyl chloride and, preferably, acetyl chloride).

The following Examples illustrate the invention.

EXAMPLE 1

25 g of myrcene in 50 ml of isopropanol were stirred for 24 hours at 20°C under argon with 0.3 g of $Rh(NO_3)_3$ and 2 ml of acetyl chloride. The mixture was distilled off from the catalyst at 0.1 Torr and the remaining terpene hydrocarbons fractionated at 55°–65°C and 10 Torr. During this fractionation the solvent was collected in a cooling trap. According to gas chromatographic analysis, the distillate (24.5 g) contained 86.5% of ocimene (cis:trans = 3.7), 9.5% of myrcene and 4% of impurities. The yield of ocimene amounted to 94% based on 91% reacted myrcene. The catalyst remained active without further working up.

EXAMPLE 2

25 g of myrcene in 50 ml of isopropanol were heated for 2 hours at 45°C with 0.3 g of $Rh(NO_3)_3$ and 2 ml of acetyl chloride. Working up according to the procedure described in Example 1 gave a 92% yield of ocimene based on 94% reacted myrcene.

EXAMPLE 3

25 g of cis-ocimene in 50 ml of isopropanol were heated for 2 hours at 50°C with 0.3 g of $Rh(NO_3)_3$ and 2 ml of acetyl chloride. After this time, the cis-trans equilibrium had adjusted itself and amounted to 3:7. The yield was 91%.

EXAMPLE 4

5 g of β-farnesene were stirred in 25 ml of absolute isopropanol with 0.1 g of $Rh(NO_3)_3$ and 0.5 ml of acetyl chloride at 20°C. After 16 hours, the equilibrium between α- and β-farnesene had adjusted itself to a ratio of 9:1. The ratio of cis-trans α-farnesene amounted to 1:3. The yield was 83%.

EXAMPLE 5

0.5 g of β-sinensal were isomerised to α-sinensal (which consisted mainly of the trans isomer) by stirring for 1 hour at 50°C under argon in 20 ml of absolute isopropanol with 0.1 g of Rh(NO$_3$)$_3$ and 0.1 g of acetyl chloride.

The products made in accordance with this invention may be employed in perfumery as odorants in known manner. The intermediates may be employed to make known odorants in accordance with known procedures.

What we claim is:

1. A process for the manufacture of unsaturated compounds of the general formula

(I)

wherein R represents the ethyl group of a grouping of the formula

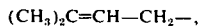
(CH$_3$)$_2$C=CH—CH$_2$—,

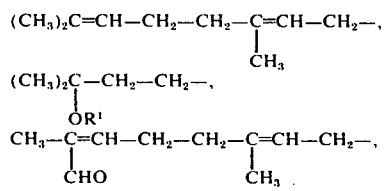
(CH$_3$)$_2$C=CH—CH$_2$—CH$_2$—C=CH—CH$_2$—,
                                          |
                                         CH$_3$ (CH$_3$)$_2$C—CH$_2$—CH$_2$—,
         |
        OR$^1$ CH$_3$—C=CH—CH$_2$—CH$_2$—C=CH—CH$_2$—,
      |                    |
     CHO                  CH$_3$

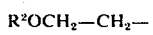
R$^2$OCH$_2$—CH$_2$— or

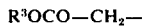
R$^3$OCO—CH$_2$— in which R$^1$ represents a hydrogen atom or a lower alkyl or lower acyl group, R$^2$ represents a lower alkyl or lower acyl group and R$^3$ represents a lower alkyl group, which process comprises treating at 0° to 50°C. a compound of the general formula

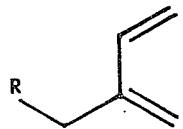
(II)

wherein R has the significance given earlier in this claim, or cis-ocimene in the presence of a lower aliphatic alcohol with Rh(NO$_3$)$_3$, and a carboxylic acid chloride selected from the group consisting of aromatic carboxylic acid chlorides and lower aliphatic carboxylic acid chlorides.

2. A process according to claim 1, wherein acetyl chloride is used as the carboxylic acid chloride.

3. A process according to claim 1, wherein isopropanol is used as the alcohol.

4. A process according to claim 1, wherein myrcene or a mixture of cis- and trans-ocimene containing less than 60% of trans isomers is used as the starting material.

5. A process for making ocimene, which comprises reacting myrcene with Rh(NO$_3$)$_3$ and acetyl chloride in the presence of isopropanol at a temperature of about 20°C for about 24 hours.

6. A process according to claim 5, wherein the reaction is conducted at about 45°C for 2 hours.

7. A process which comprises reacting cis-ocimene in isopropanol for about 2 hours at 50°C with Rh(NO$_3$)$_3$ and acetyl chloride.

8. A process which comprises reacting β-farnesene in isopropanol with Rh(NO$_3$)$_3$ and acetyl chloride at about 20°C for about 16 hours.

9. A process which comprises reacting β-sinensal for about 1 hour at around 50°C under argon in the presence of isopropanol with Rh(NO$_3$)$_3$ and acetyl chloride.

* * * * *